United States Patent
Ravuna et al.

(10) Patent No.: US 11,278,233 B2
(45) Date of Patent: Mar. 22, 2022

(54) METHOD AND APPARATUS TO FIND ABNORMAL ACTIVATIONS IN INTRA-CARDIAC ELECTROCARDIOGRAMS BASED ON SPECIFICITY AND SENSITIVITY

(71) Applicant: Biosense Webster (Israel) Ltd., Yokneam (IL)

(72) Inventors: Eliyahu Ravuna, Kiryat Ata (IL); Yaron Kadoshi, Hosha'aya (IL); Refael Itah, Tel Aviv (IL); Elad Nakar, Timrat (IL); Michal Alroy Levy, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 118 days.

(21) Appl. No.: 16/685,496

(22) Filed: Nov. 15, 2019

(65) Prior Publication Data
US 2021/0145301 A1    May 20, 2021

(51) Int. Cl.
  *A61B 5/366* (2021.01)
  *A61B 5/283* (2021.01)
  *A61B 5/00* (2006.01)

(52) U.S. Cl.
  CPC ............. *A61B 5/366* (2021.01); *A61B 5/283* (2021.01); *A61B 5/7264* (2013.01)

(58) Field of Classification Search
  None
  See application file for complete search history.

(56) References Cited

U.S. PATENT DOCUMENTS

| | | | |
|---|---|---|---|
| 10,383,534 B2 | 8/2019 | Botzer et al. | |
| 10,398,331 B2 | 9/2019 | Relan et al. | |
| 10,912,472 B2 * | 2/2021 | Finlay | A61B 5/25 |
| 2012/0184863 A1 | 7/2012 | Harlev | |
| 2014/0200473 A1 * | 7/2014 | Zeng | A61B 5/486 |
| | | | 600/523 |

(Continued)

FOREIGN PATENT DOCUMENTS

WO    WO2017192294 A1    11/2017

OTHER PUBLICATIONS

Nguyen, M. P. et al. "A new approach for automated location of active segments in intracardiac electrograms." (2009).

(Continued)

*Primary Examiner* — Kennedy Schaetzle
(74) *Attorney, Agent, or Firm* — Volpe Koenig

(57) ABSTRACT

Methods, apparatus, and systems for medical procedures are disclosed herein and include detecting points of an intra-cardiac area that exhibits abnormal activations, such as local abnormal ventricular activations (LAVAs). Points that exhibit such abnormal activations may be referred to as seed points that are identified during a first step of the process disclosed herein. The seed points may be identified using one or more inputs such as unipolar and bipolar mapping channels, body surface ECGs, past activations, neighboring points and the like during the first step which prioritizes high specificity over sensitivity. During a second step which prioritizes high sensitivity, electrical activations of neighboring points near the seed points are analyzed to determine if the activations are similar (e.g., have a similar time) as the abnormal activations corresponding to the corresponding seed points.

20 Claims, 10 Drawing Sheets

(56) References Cited

U.S. PATENT DOCUMENTS

| | | | |
|---|---|---|---|
| 2017/0225001 A1* | 8/2017 | Zaidi | A61N 1/3937 |
| 2018/0055401 A1* | 3/2018 | Wang | A61B 5/746 |
| 2018/0085021 A1* | 3/2018 | Chakravarthy | A61B 5/316 |
| 2018/0365828 A1* | 12/2018 | Mansi | G16H 30/20 |
| 2020/0163582 A1* | 5/2020 | Hayam | A61B 5/743 |

OTHER PUBLICATIONS

"Classification: ROC Curve and AUC," Google Machine Learning Crash Course, https://developers.google.com/machine-learning/crash-course/classification/roc-and-auc , Available at: https://web.archive.org/web/20190614221737/https://developers.google.com/machine-learning/crash-course/classification/roc-and-auc (Jun. 14, 2019).
European Search Report for corresponding EPA No. 20207557.8 dated Apr. 7, 2021.

* cited by examiner

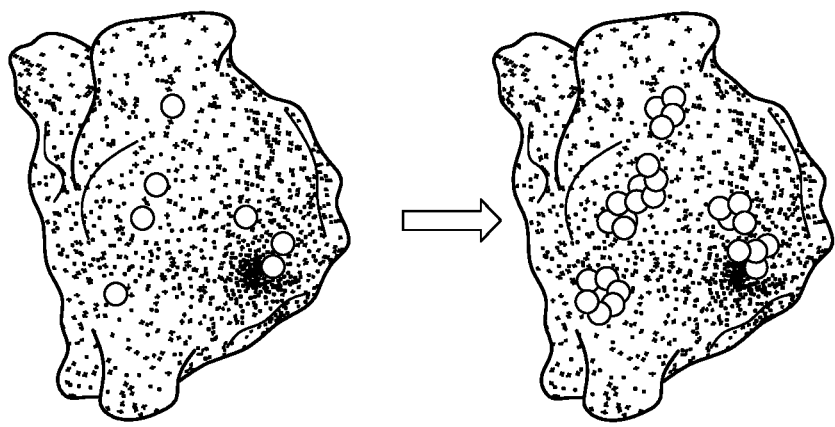
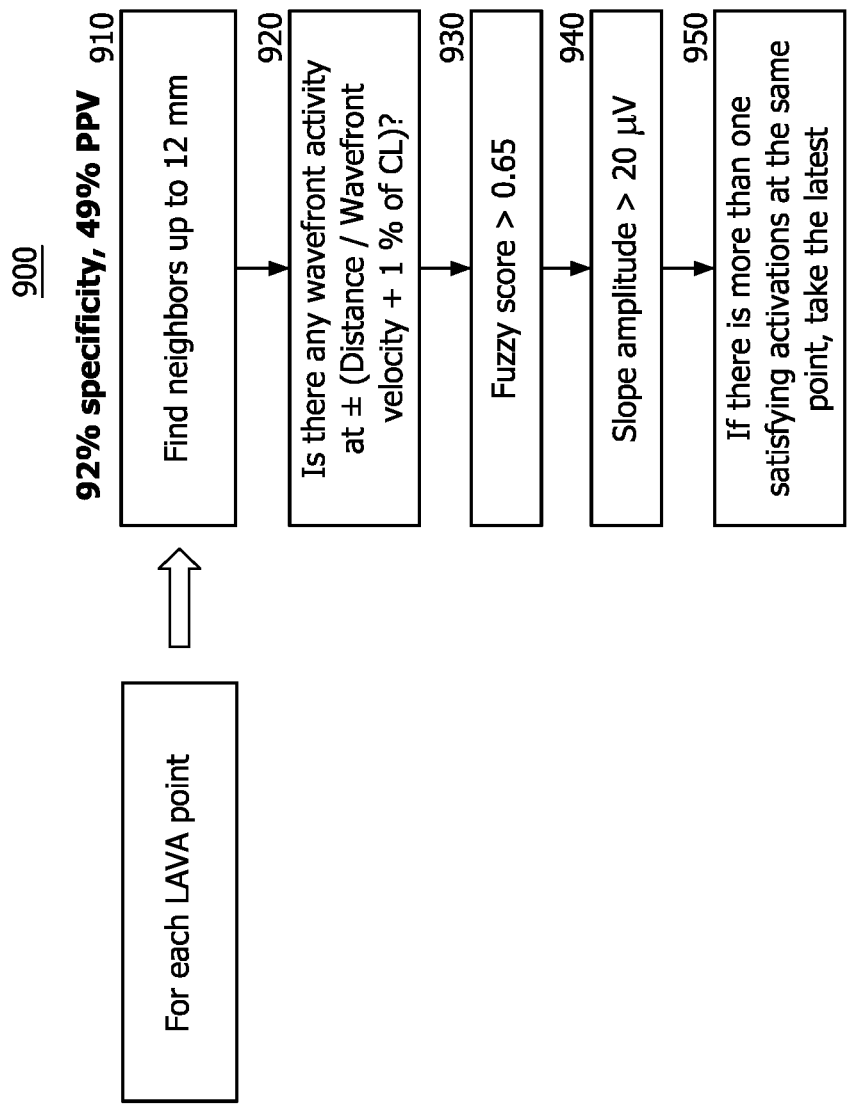
FIG. 9

METHOD AND APPARATUS TO FIND ABNORMAL ACTIVATIONS IN INTRA-CARDIAC ELECTROCARDIOGRAMS BASED ON SPECIFICITY AND SENSITIVITY

FIELD OF INVENTION

The present application provides systems, apparatuses, and methods for detecting abnormal intra-cardiac activity.

BACKGROUND

Medical conditions such as cardiac arrhythmia (e.g., atrial fibrillation (AF)) are often diagnosed and treated via intra-body procedures. For example, electrical pulmonary vein isolation (PVI) from the left atrial (LA) body is performed using ablation for treating AF. Such intra-body procedures rely on the detection of areas of concern within an intra-body organ, such as a heart.

Detecting abnormal or targeted electrical activity for an intra-cardiac area may provide areas of the heart to be ablated, in order to prevent the abnormal or targeted electrical activity from propagating within the heart and, thus, mitigating the possibility of a cardiac condition such as cardiac arrhythmia.

SUMMARY

Methods, apparatus, and systems for medical procedures are disclosed herein and include detecting points of an intra-cardiac area that exhibit abnormal activations, such as local abnormal ventricular activations (LAVAs). Points that exhibit such abnormal activations may be referred to as seed points that are identified during a first step of the process disclosed herein. The seed points may be identified using one or more inputs such as unipolar and bipolar mapping channels, body surface ECGs, past activations neighboring points and the like during the first step which prioritizes high specificity over sensitivity. During a second step which prioritizes high sensitivity, electrical activations of neighboring points near the seed points are analyzed to determine if the activations are similar (e.g., have a similar time) as the abnormal activations corresponding to the respective seed points.

BRIEF DESCRIPTION OF THE DRAWINGS

A more detailed understanding can be had from the following description, given by way of example in conjunction with the accompanying drawings wherein:

FIG. 9 is a diagram for identifying neighboring points of abnormal activity based on seed points.

DETAILED DESCRIPTION

Identifying complex electrocardiogram (ECG) activations, such as local abnormal ventricular activations (LAVAs), fractionations and/or late potentials with high sensitivity and high specificity can be challenging. Techniques such as feature extraction and dynamic thresholding can be used to identify such complex ECG activations and may be implemented based on one or more inputs and/or features. However, such techniques may sacrifice specificity (i.e., a true negative rate) when attempting to improve sensitivity (i.e., a true positive rate).

According to exemplary embodiments of the present invention, a catheter may be inserted into an intra-cardiac chamber of a patient's heart. The catheter may include one or more electrodes which may provide electrical activity for areas of the intra-cardiac chamber that are in contact with the one or more electrodes. Seed points corresponding to abnormal activity may be identified with high specificity. Subsequently, neighboring points to the seed points may be identified with high sensitivity. One or more complex ECG activations such as LAVAs may be determined based on the seed points and the neighboring points. Notably, the techniques disclosed herein may be implemented to increase the sensitivity of results without sacrificing the specificity.

According to exemplary embodiments of the present invention, at a first step, abnormal activations of endocardiac or epicardiac tissue are identified with a high specificity, as further disclosed herein. At a second step after identifying abnormal activations, points neighboring the identified abnormal activations are evaluated to determine if they contain activations at times similar to the identified abnormal activations. If a determination is made that one or more points neighboring the identified abnormal activations contain activations at a time similar to the identified abnormal activations, then such one or more neighboring points are also marked as having abnormal activations.

Figure 1:
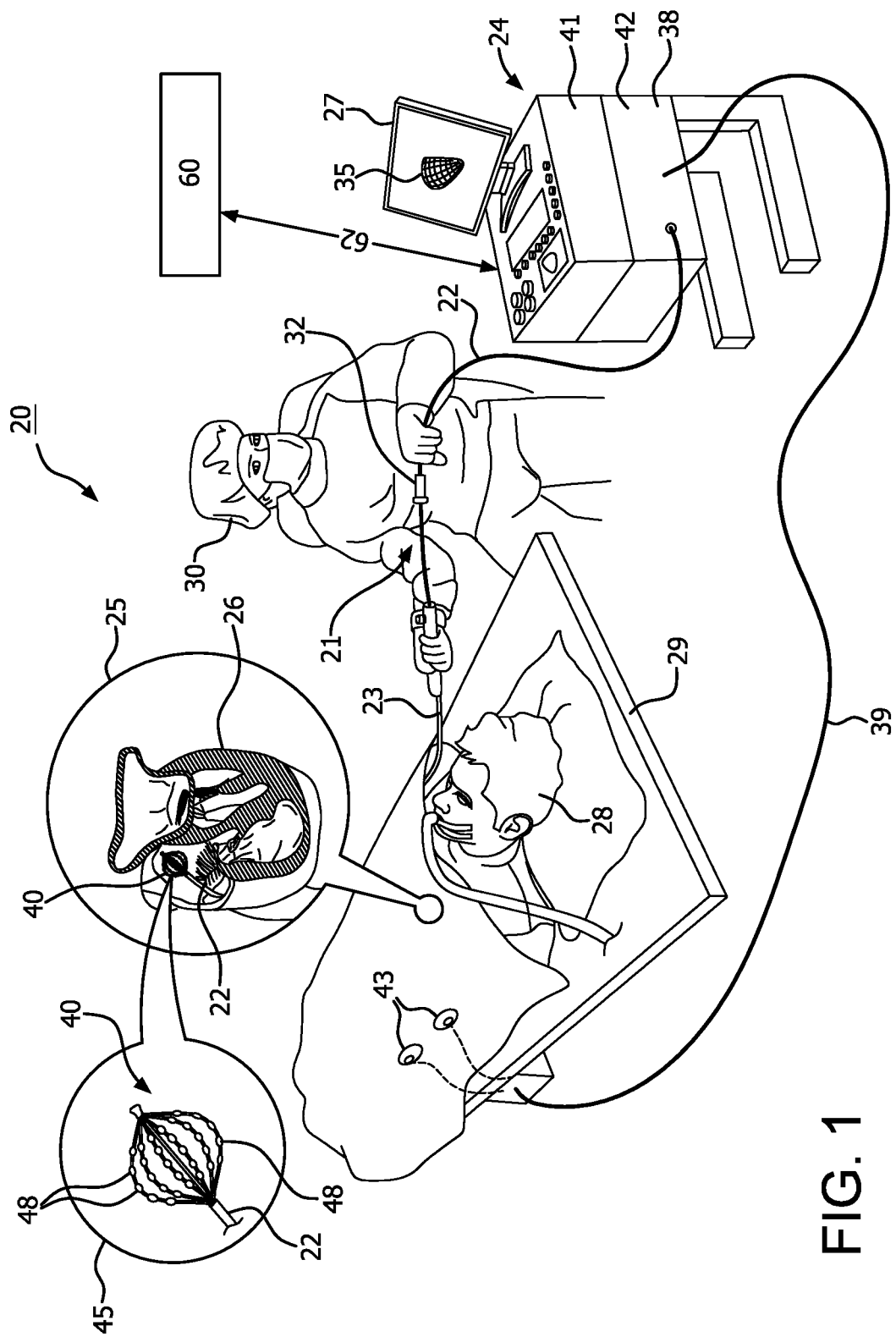
FIG. 1 is a diagram of an exemplary system in which one or more features of the disclosure subject matter can be implemented.

FIG. 1 is a diagram of an exemplary mapping system 20 in which one or more features of the disclosed subject matter can be implemented. Mapping system 20 may include a device, such as a catheter 40, that is configured to obtain electrical activity data in accordance with an exemplary embodiment of the present invention. Although catheter 40 is shown to have a basket shape, it will be understood that a catheter of any shape that includes one or more elements (e.g., electrodes) may be used to implement the exemplary embodiments disclosed herein. Mapping system 20 includes a probe 21, having a shaft 22 that may be navigated by a medical professional 30 into a body part, such as heart 26, of a patient 28 lying on a table 29. As shown in FIG. 1, medical professional 30 may insert shaft 22 through a sheath 23, while manipulating the distal end of shaft 22 using a manipulator 32 near the proximal end of the catheter and/or deflection from the sheath 23. As shown in an inset 25, catheter 40 may be fitted at the distal end of shaft 22. Catheter 40 may be inserted through sheath 23 in a collapsed state and may be then expanded within heart 26.

According to an exemplary embodiment of the present invention, the catheter 40 may be configured to obtain electrical activity within an intra-cardiac chamber of the heart 26. Inset 45 shows catheter 40 in an enlarged view, inside a cardiac chamber of heart 26. As shown, catheter 40 may include an array of elements (e.g., electrodes 48) coupled onto splines that form the shape of the catheter 40. The elements (e.g., electrodes 48) may be any elements configured to obtain electrical activity and may be electrodes, transducers, or one or more other elements. It will be understood that although one catheter 40 is shown, multiple catheters may be used to collect electrical activity of an intra-body organ such as the heart 26.

According to exemplary embodiments disclosed herein, electrical activity may be any applicable electrical signals that may be measured based on one or more thresholds and may be sensed and/or augmented based on signal to noise ratios and/or other filters. A catheter, such as catheter 40 may also be configured to sense additional biometric data in addition to electrical activity. The data collected by catheter 40 may include one or more of local activation times (LATs), topology, bipolar mapping, unipolar mapping, body surface electrode-based mapping, dominant frequency, impedance, or the like. Further, the catheter 40 may be used to obtain spatial information about an intra-body organ. Local activation times may be points in time of a threshold activity corresponding to a local activation, calculated based on a normalized initial starting point. A topology may correspond to the physical structure of a body part or a portion of a body part and may correspond to changes in the physical structure relative to different parts of the body part or relative to different body parts. A dominant frequency may be a frequency or a range of frequencies that is prevalent at a portion of a body part and may be different in different portions of the same body part. For example, the dominant frequency of a pulmonary vein of a heart may be different than the dominant frequency of the right atrium of the same heart. Impedance may be the resistance measurement at a given area of a body part and may be calculated as a standalone value, based on a frequency, and/or in combination with additional considerations such as blood concentration.

As shown in FIG. 1, the probe 21 and catheter 40 may be connected to a console 24. Console 24 may include a processor 41, such as a general-purpose computer, with suitable front end and interface circuits 38 for transmitting and receiving signals to and from catheter 40, as well as for controlling the other components of mapping system 20. In some exemplary embodiments of the present invention, processor 41 may be further configured to receive electrical activity data, allocate clusters of points at different times and provide a visual indication from a first cluster of points to a related second cluster of points. According to exemplary embodiments of the present invention, rendering data may be used to provide the medical professional 30 with a rendering of one or more body parts on a display 27, e.g., a body part rendering 35. According to an exemplary embodiment of the present invention, the processor 41 may be external to the console 24 and may be located, for example, in the catheter, in an external device, in a mobile device, in a cloud-based device, or may be a standalone processor.

As noted above, processor 41 may include a general-purpose computer, which may be programmed in software to carry out the functions described herein. The software may be downloaded to the general-purpose computer in electronic form, over a network, for example, or it may, alternatively or additionally, be provided and/or stored on non-transitory tangible media, such as magnetic, optical, or electronic memory. The exemplary configuration shown in FIG. 1 may be modified to implement the embodiments disclosed herein. The disclosed exemplary embodiments may similarly be applied using other system components and settings. Additionally, mapping system 20 may include additional components, such as elements for sensing biometric patient data, wired or wireless connectors, processing and display devices, or the like.

According to an exemplary embodiment of the present invention, a display connected to a processor (e.g., processor 41) may be located at a remote location such as a separate hospital or in separate healthcare provider networks. Additionally, the mapping system 20 may be part of a surgical system that is configured to obtain anatomical and electrical measurements of a patient's organ, such as a heart, and performing a cardiac ablation procedure. An example of such a surgical system is the Carto® system sold by Biosense Webster.

The mapping system 20 may also, and optionally, obtain biometric data such as anatomical measurements of the patient's heart using ultrasound, computed tomography (CT), magnetic resonance imaging (MRI) or other medical imaging techniques known in the art. The mapping system 20 may obtain electrical measurements using catheters, electrocardiograms (ECGs) or other sensors that measure electrical properties of the heart. The biometric data including anatomical and electrical measurements may then be stored in a local memory 42 of the mapping system 20, as shown in FIG. 1. Notably, memory 42 may store biometric data for multiple different modalities at the same time. The biometric data may be transmitted to the processor 41 from the memory 42. Alternatively, or in addition, the biometric data may be transmitted to a server 60, which may be local or remote, using a network 62.

Network 62 may be any network or system generally known in the art such as an intranet, a local area network (LAN), a wide area network (WAN), a metropolitan area network (MAN), a direct connection or series of connections, a cellular telephone network, or any other network or medium capable of facilitating communication between the mapping system 20 and the server 60. The network 62 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 62.

In some instances, the server 60 may be implemented as a physical server. In other instances, server 60 may be implemented as a virtual server a public cloud computing provider (e.g., Amazon Web Services (AWS)®).

Control console 24 may be connected, by a cable 39, to body surface electrodes 43, which may include adhesive skin patches that are affixed to the patient 28. The processor 41, in conjunction with a current tracking module, may determine position coordinates of the catheter 40 inside the body part (e.g., heart 26) of a patient. The position coordinates may be based on impedances or electromagnetic fields measured between the electrodes 43 and the electrodes 48 or other electromagnetic components of the catheter 40.

Processor 41 may comprise real-time noise reduction circuitry typically configured as a field programmable gate array (FPGA), followed by an analog-to-digital (A/D) ECG (electrocardiograph) or EMG (electromyogram) signal conversion integrated circuit. The processor 41 may pass the signal from an A/D ECG or EMG circuit to another processor and/or can be programmed to perform one or more functions disclosed herein.

Control console 24 may also include an input/output (I/O) communications interface that enables the control console to transfer signals from, and/or transfer signals to electrodes 48 and electrodes 43. Based on signals received from electrodes 48 and/or electrodes 43, processor 41 may generate rendering data that enables a display, such as display 27 to render a body part, such as a body part rendering 35 and biometric data of multiple modalities as part of the body part rendering 35.

During a procedure, processor 41 may facilitate the presentation of a body pare rendering 35, including one or more clusters of points that are active at a given time. The processor 41 may identify the one or more clusters at the given time as well as one or more other related or unrelated clusters at a subsequent time. The processor 41 may also determine a propagation route based on the two or more related clusters of points and provide a visual indication of the propagation route accordingly. The electrical activity may be stored in a memory 42 and the processor 41 may have access to the electrical activity stored in memory 42 to determine the clusters of point and the corresponding propagation route(s). The propagation route(s) may be provided to a medical professional 30 on a display 27.

Memory 42 may comprise any suitable volatile and/or non-volatile memory, such as random-access memory or a hard disk drive. In some exemplary embodiments of the present invention, medical professional 30 may be able to manipulate a body part rendering 35 using one or more input devices such as a touch pad, a mouse, a keyboard, a gesture recognition apparatus, or the like. In alternative exemplary embodiments of the present invention, display 27 may include a touchscreen that can be configured to accept inputs from medical professional 30, in addition to presenting a body part rendering 35, including the propagation route(s).

Figure 2:
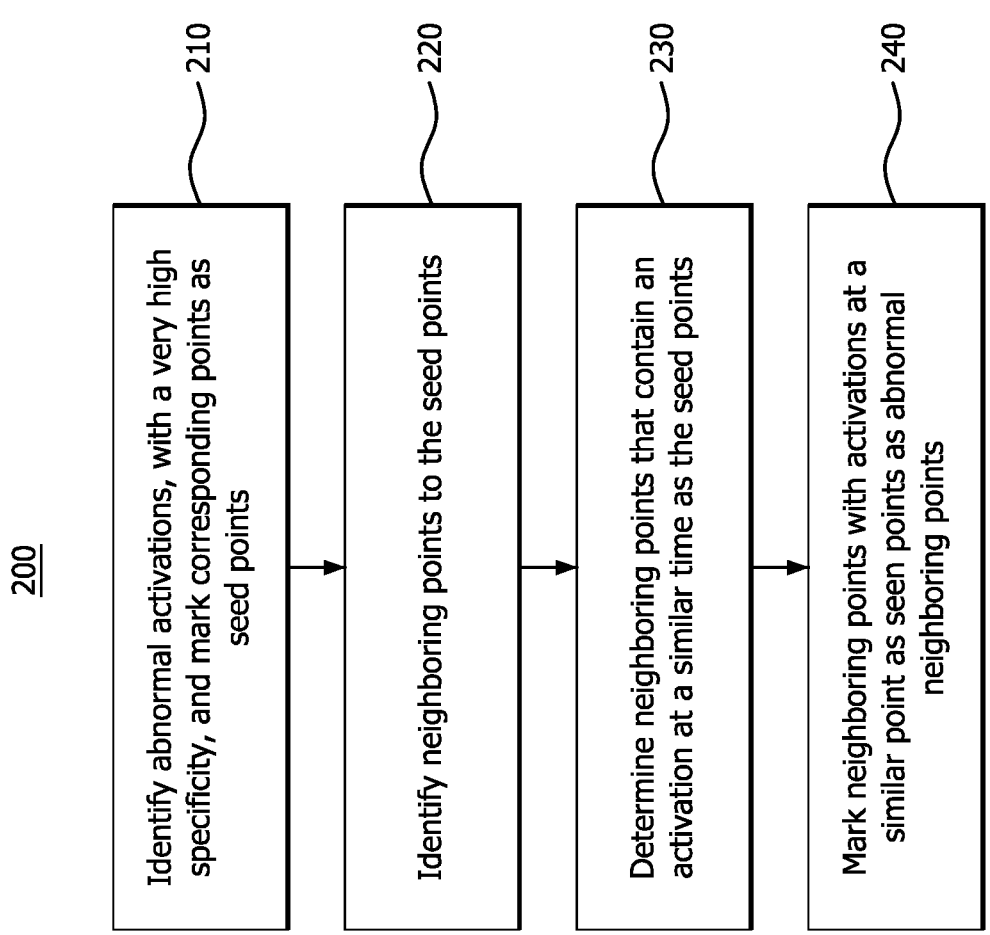
FIG. 2 is a process for identifying abnormal activations.

FIG. 2 shows a process 200 for identifying and marking abnormal activation points, according to exemplary embodiments of the present invention. Seed points, as referenced herein, are points of an intra-cardiac chamber that exhibit abnormal activations. Such seed points are identified at step 210 of the process 200 with high sensitivity such that true positive rate is emphasized when identifying such seed points. The receiver operating characteristics (ROC) curve, as understood in the art, is adjusted to favor specificity when identifying the seed points at step 210. Subsequently at steps 220-240, higher sensitivity is emphasized by identifying neighboring points that exhibit activations at a similar time to the abnormal activations of a corresponding seed point, as further described herein. Notably, by identifying the neighboring points at step 220-240, the techniques disclosed herein effectively enlarge the area around the identified seed points by identifying abnormal activations corresponding to the neighboring points. The ROC curve is adjusted to favor sensitivity when identifying the neighboring points at steps 220-240. The result of the process 200 is to identify abnormal activation areas of endocardiac or epicardiac tissue with a high level of specificity (e.g., through step 210) and a high level of sensitivity (e.g., through steps 220-240).

In step 210 of the process 200 of FIG. 2, one or more abnormal activation points are identified with a high level of specificity. The abnormal activation points identified at step 210 may be referred to as seed points to distinguish them from neighboring points that are also identified as having abnormal activations, as further disclosed herein.

Figure 3:
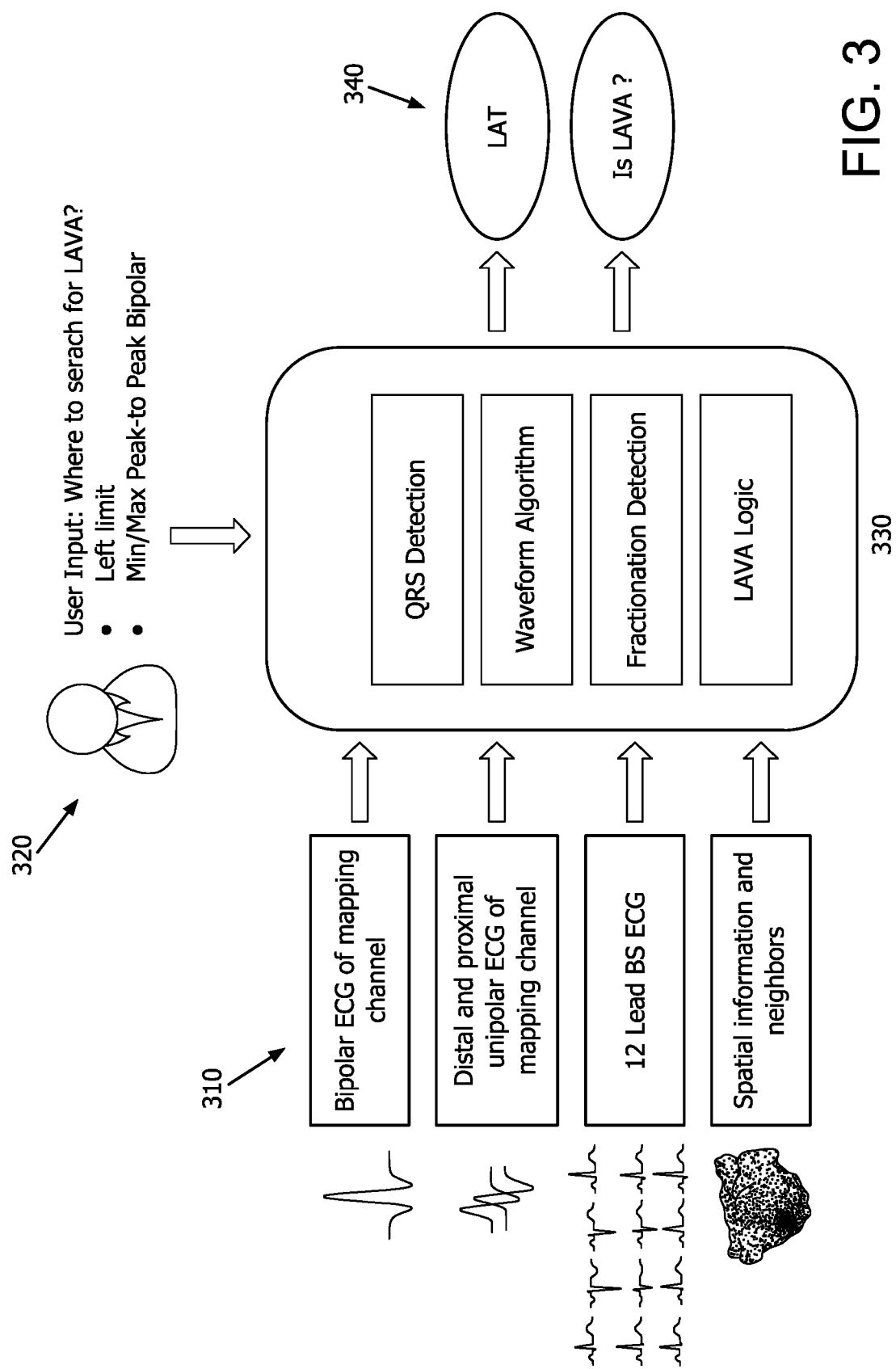
FIG. 3 is a diagram for receiving intra-cardiac inputs to determine abnormal activity.

FIG. 3 shows inputs 310 (e.g., input information) that may be applied to determine abnormal activation points from an intra-cardiac chamber. The inputs 310 may include, but are not limited to, a bipolar ECG of a mapping channel, a distal and/or proximal unipolar ECG of a mapping channel, a multi-lead (e.g., 12 lead) body surface (BS) ECG, special information and neighboring point information, or the like. One or more of the inputs 310 may be received by a processor such as processor 41 of FIG. 1. Additionally, user input 320 may be provided to a processor, such as processor 41 and may include location information for areas to exclude when identifying abnormal activations and may include limits, and/or minimum and maximum voltages.

As shown in FIG. 3, the processor may execute one or more techniques 330 (e.g., analysis modules) based on the inputs 310 and/or the user inputs 320. The one or more techniques 330 (e.g., analysis modules) may include QRS detection, wavefront algorithm(s), fractionation detection, LAVA logic, or the like. The application of the one or more techniques 330 may provide electrical activity 340 which may include LAT values and may also include a determination of whether a point is exhibiting LAVAs.

Figure 4:
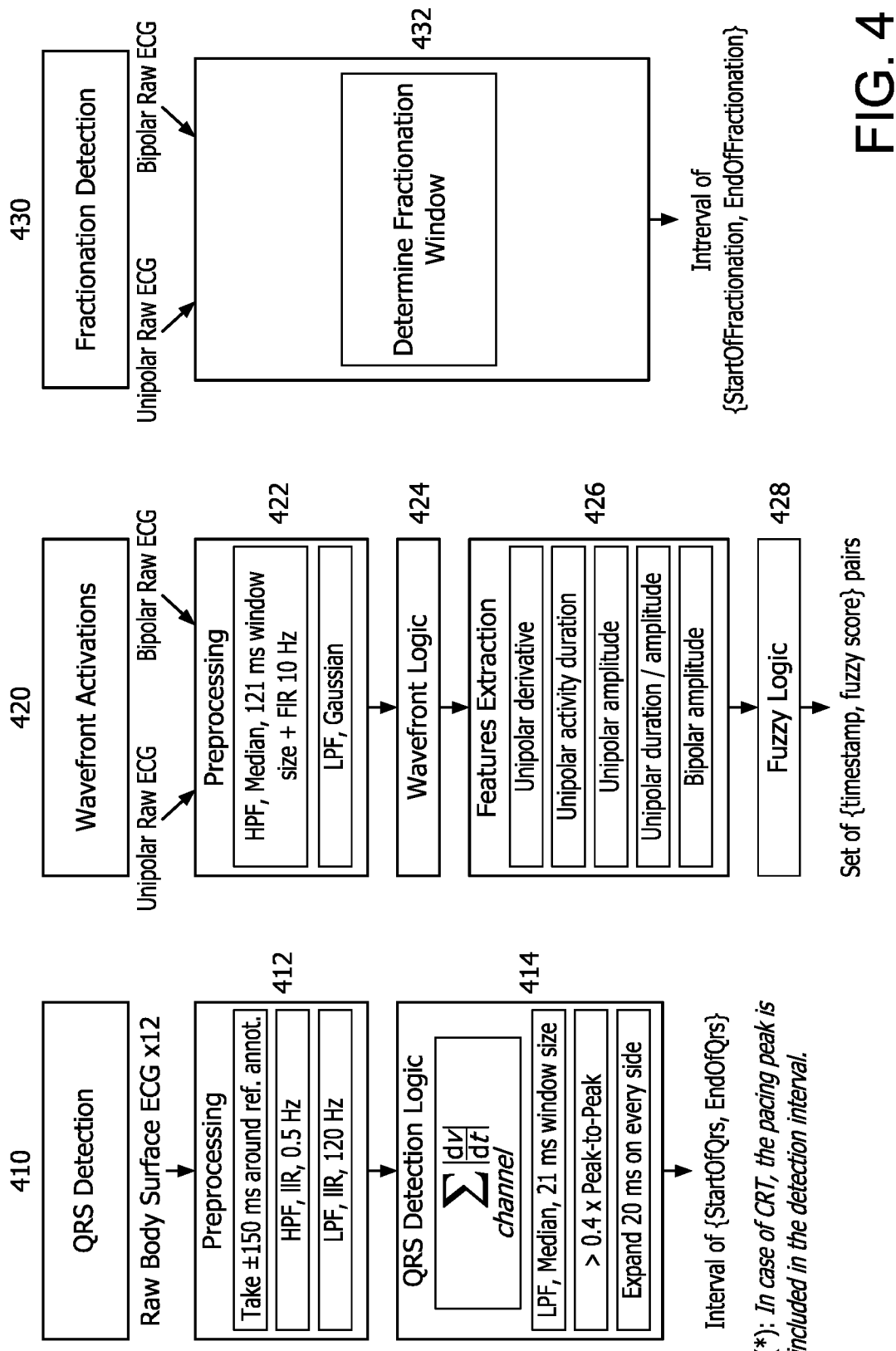
FIG. 4 is a diagram for applying intra-cardiac inputs to determine abnormal activity.

FIG. 4 provides additional information regarding application of the inputs 310 of FIG. 3. The QRS detection 410, wavefront activations 420, and fractionation detection 430 of FIG. 4 may be applied, as further provided in FIG. 8, when determining seed points at step 210 of FIG. 2.

QRS detection 410 of FIG. 4 may include a preprocessing step 412 and a QRS detection logic step 414. The QRS detection 410 may be based on the electrical activity received from the electrodes of a catheter, such as catheter 40 of FIG. 1, relative to baseline electrical activity determined using one or more BS electrodes attached external to a patient's body. For example, the processor, such as processor 41, may receive baseline electrical activity from a number (e.g., twelve) of BS electrodes and may extract QRS signals based on comparing the electrical activity received from the electrodes of a catheter to the baseline electrical activity.

During the preprocessing step 412, electrical activity measurements within a given amount of time (e.g., 150 ms) around a reference annotation may be collected. A high pass filter and/or a low pass filter may be applied to the received electrical activity. According to an example, the high pass filter may be applied with a 0.5 Hz threshold and the low pass filter may be applied with a 120 Hz threshold.

During the QRS detection step 414, QRS signals may be determined based on the change in voltage over time of the received electrical activity as provided during the preprocessing step 412. An additional low pass filter may be applied using median measurements within a window of time (e.g., 21 ms). Voltages with a peak to peak measurement of greater than a given voltage (e.g., 0.4 mV) may be identified and additional electrical activity for an additional time period (e.g., 20 ms before and after the peak) may be observed. The QRS detection logic step 414 may provide intervals of the start of a QRS signal and end of QRS signal (StartOfQrs, EndOfQrs). Notably, the intervals may be used in determining whether electrical activity at a point on an intra-cardiac surface exhibits abnormal activations (i.e., is a seed point), as further disclosed herein.

As shown in FIG. 4, wavefront activations 420 may be determined based on raw unipolar ECG signals and/or bipolar ECG signals. During a preprocessing step 422, a high pass filter may be applied using median measurements of a given time window (e.g., 121 ms window) with a finite impulse response (FIR) filter at a given frequency (10 Hz).

The prepossessing input may be provided to a wavefront logic 424, and a feature extraction step 426 may be applied to the output of the wavefront logic 424. The feature extraction step 426 may provide one or more of a unipolar derivative, unipolar activity duration, unipolar amplitude, unipolar duration over amplitude, and/or a bipolar amplitude. The output of the feature extraction step 426 may be applied to a fuzzy logic step 428 which results in fuzzy scores as sets of (timestamp, fuzzy score) pairs for given points on an intra-cardiac surface. Notably, the sets of (timestamp, fuzzy score) pairs may be used in determining whether electrical activity at a point on an intra-cardiac surface exhibits abnormal activations (i.e., is a seed point), as further disclosed herein. A fuzzy score may be calculated based on the features including the height, weight and/or slope of a negative deflection of a bipolar signal and features including the height, weight and/or slope of the negative deflection of a unipolar signal. Each such feature may affect the fuzzy score according to a different fuzzy membership function. The iterative fuzzy score of each feature may be multiplied to calculate the final fuzzy score of a given point.

As shown in FIG. 4, fractionation detection 430 may be determined based on raw unipolar ECG signals and/or bipolar ECG signals. During a fractionation window detection step 432, a fractionation window for electrical activity at a point on an intra-cardiac surface may be determined. The fractionation window may be determined based on the raw unipolar ECG signals and/or bipolar ECG signals and may be determined based on any applicable technique to detect fractionation windows. Such techniques may include, but are not limited to, applying one or more steps such as preprocessing, differentiation and squaring, moving window integration, thresholding, post processing, evaluation with a non-linear energy operator (NELO), Gaussian low pass filtering, or a combination thereof. The output of the fractionation window detection step 432 may provide intervals of the start of a fractionation window and the end of a fractionation window (e.g., (StartOfFractionation, EndOfFractionation). Notably, the intervals of the start of a fractionation window and the end of a fractionation window may be used in determining whether electrical activity at a point on an intra-cardiac surface exhibits abnormal activations (i.e., is a seed point), as further disclosed herein. When fractionation windows are compared, in order to be considered similar, a specific intersection percentage of the fractionation window may be required between two points being compared.

Figure 5:
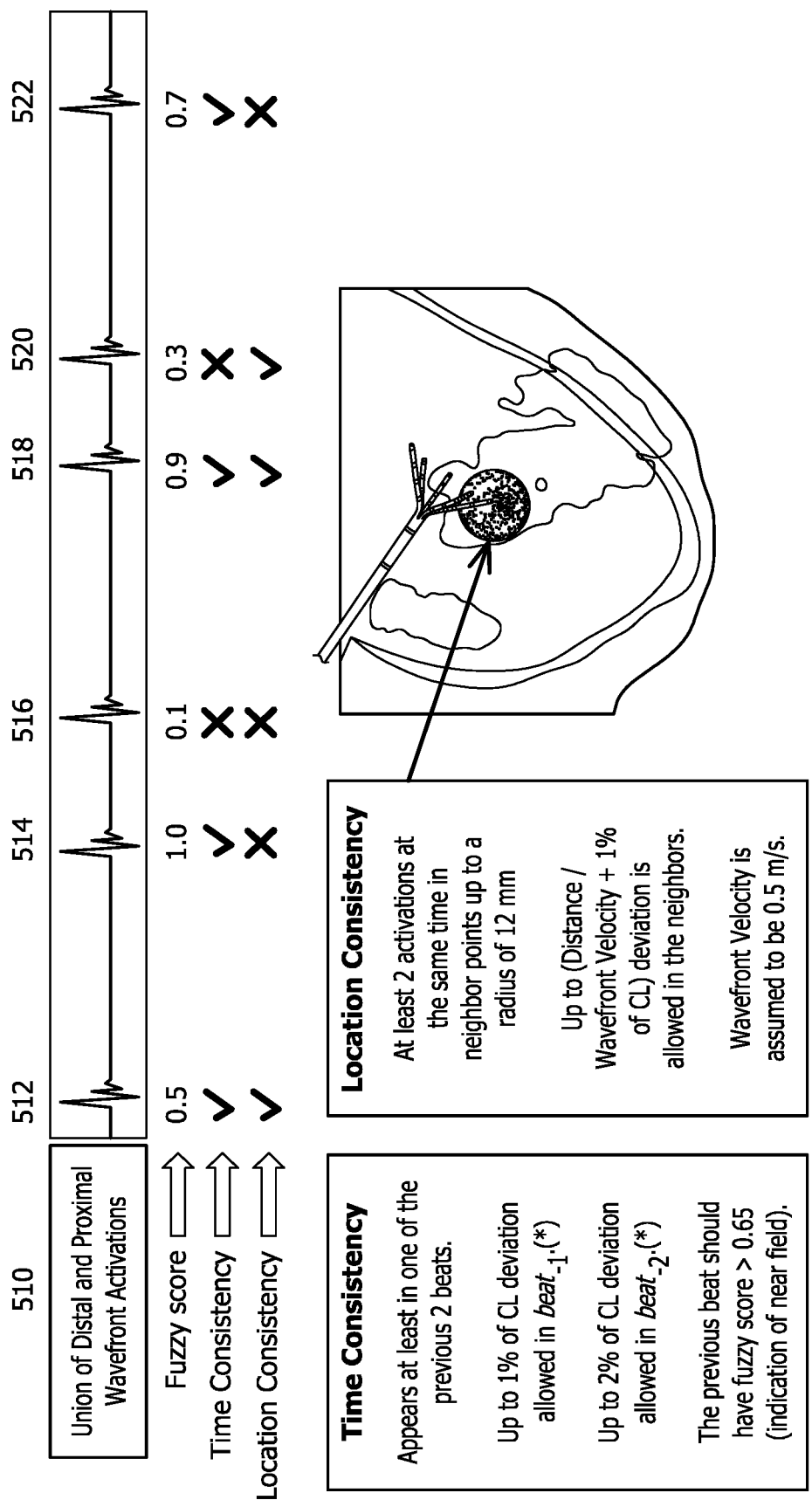
FIG. 5 is a diagram for determining abnormal activity based on intra-cardiac inputs.

As shown in FIG. 5, a processor, such as processor 41 of FIG. 1, may determine if electrical activity at a point on an intra-cardiac surface is abnormal based on one or more of a fuzzy score, time consistency, and location consistency. As shown in FIG. 5, for each union of distal and proximal wavefront activations 510, including activations 512, 514, 516, 518, 520, and 522, the processor may determine the fuzzy score, whether time consistency exists between adjacent beats, and whether location consistency exists between neighboring points. A threshold fuzzy score (e.g., 0.65) may be applied such that a calculated fuzzy score for a given point on an intra-cardiac surface corresponds to abnormal electrical activity if it exceeds the threshold fuzzy score.

According to exemplary embodiments of the present invention, time consistency may exist for a detected electrical activation if the activation was present in one or more of the previous cycles. The existence of the detected electrical activation in one or more of the previous cycles may indicate that the detected electrical activation is generated by the heart and is not noise. Time consistency may be detected if the electrical activation was present in a previous cycle with a tolerance of up to 1% deviation for the previous cycle, a tolerance of up to 2% deviation for two cycles prior to the given electrical activation, and so forth. To clarify, time consistency may exist if electrical activity detected during a given cycle is also present at the same time in a previous cycle with a tolerance deviation of 1% deviation of time in the previous cycle. Similarly, time consistency may exist if electrical activity detected during a given cycle is also present at the same time two cycles prior to the given cycle, with a tolerance amount of 2% deviation of time in the two cycles prior to the given cycle. As shown in FIG. 5, activations 512, 514, 518, and 522 may exhibit time consistency.

At step 220 of the process 200 of FIG. 2, electrical activity of neighboring points within a given threshold distance (e.g., 12 mm) of the seed points identified in step 210, may be identified. At step 230, a determination may be made that one or more of the neighboring points exhibit abnormal electrical activity similar to the corresponding seed point identified at step 210. The neighboring points that exhibit abnormal electrical activity may be determined based on the same process as applied at step 210, and as disclosed herein. At step 240, the neighboring point(s) that exhibit abnormal activity may be marked as abnormal neighboring points.

According to exemplary embodiments of the present invention, neighboring points may be identified, at step 220, up to a given threshold distance (e.g., 12 mm) which may be a constant or may be user-defined. The given threshold distance may be the Euclidean distance between two points. Alternatively, the given threshold distance may be the shortest path between two points on an intra-cardiac surface as determined, for example, by Dijkstra's algorithm.

According to an exemplary embodiment, an area or a number of points may be excluded from being considered as seed points and/or abnormal neighboring points. Such area or number of points may be excluded based on user input such as if a user marks anatomical locations and/or points near anatomical locations to be excluded. Such excluded points may be part of a Bundle of His, where a bundle of His includes wide, fast-conducting muscle fibers that carry a cardiac impulse through an insulating annulus fibrosus into the fibrous upper part of the ventricular septum.

As shown in FIG. 5, the location consistency indication for neighboring points of a seed point may be determined. The location consistency may provide an indication that the abnormal electrical activity exhibited at the seed point is also present at the neighboring points. Notably, for neighboring points proximate to the seed point, abnormal electrical activity may be expected to be exhibited at a similar time as that of the seed point. Location consistency may be determined based on the distance between the seed point and a neighboring point divided by the wavefront velocity plus a percentage (e.g., 1%) of the cycle length (CL) for a given cycle (i.e., similar time=(Distance/Wavefront Velocity)+1% CL) such that if the neighboring point exhibits electrical activations within the similar time as the electrical activations of the seed point, then location consistency may be present. As indicated in the equation provided above, and in general, the tolerance (e.g., 1% CL) to consider two activation times as similar times may be a function of the CL such that if the CL is short, less deviation is allowed and if the CL is long then more deviation is allowed. A default wavefront velocity of 0.5 mm/ms may be applied especially if the actual wavefront velocity is unknown. The tolerance of a percentage (e.g., 1%) of a CL may account for deviations in wavefront velocity. As examples, the wavefront velocity in healthy tissue may be 0.9 mm/ms and the wavefront velocity in scar tissue may be 0.1 mm/ms. As shown in FIG. 5, activations 512, 518, and 520 may exhibit location consistency such that at least two activations at a similar time are present within neighboring points of the seed point. Notably, location consistency may indicate that the abnormal electrical activity at a seed point is confirmed by the electrical activity of the neighboring points. According to an embodiment, the wavefront velocity may be 1 mm/ms. According to an embodiment, the similar time may be a pre-determined value or a user-provided value. A neighboring point with electrical activation(s) at a similar time as the seed point may be considered and abnormal neighboring point such that the seed point and the abnormal neighboring point(s) may correspond to an area of complex ECG activations (e.g., LAVAs, fractionations, late potentials, etc.)

According to exemplary embodiments, to be considered similar times when considering activation times for two or more points, the onset or the center of an activation window may be compared, the threshold may apply to the center, or to the onset of the signal. In the case of fractionated ECG signals, the activation time may be a window and not a single point. Further, the duration of activations may also need to be similar when considering similar times of activations. According to embodiments, the allowed difference in activation times to be considered similar times may be a function of the peak-to-peak voltages such that high a peak-to-peak bipolar voltage may correspond to healthy tissue with a relatively high wavefront velocity, as disclosed herein. Similarly, low peak-to-peak bipolar voltages may correspond to unhealth tissue, such as scar tissue, with a relatively low wavefront velocity, as disclosed herein. Accordingly, for high peak-to-peak voltage areas, the activation times may propagate faster between neighboring points and, conversely, may propagate slower between neighboring points of low peak-to-peak voltage areas.

According to exemplary embodiments, when identifying neighboring points with abnormal activity (e.g., steps 220-240 of process 200 of FIG. 2), the radius to find neighboring points may be defined as a relatively large number, but the ROC may be adjusted to favor less sensitivity and more specificity for points further away from the seed point found in step 210. It will be understood that at any point on the ROC curve, the time of a given activation on a neighboring point is still needed to be at a similar time, as disclosed herein, to a corresponding seed point.

Figure 6:
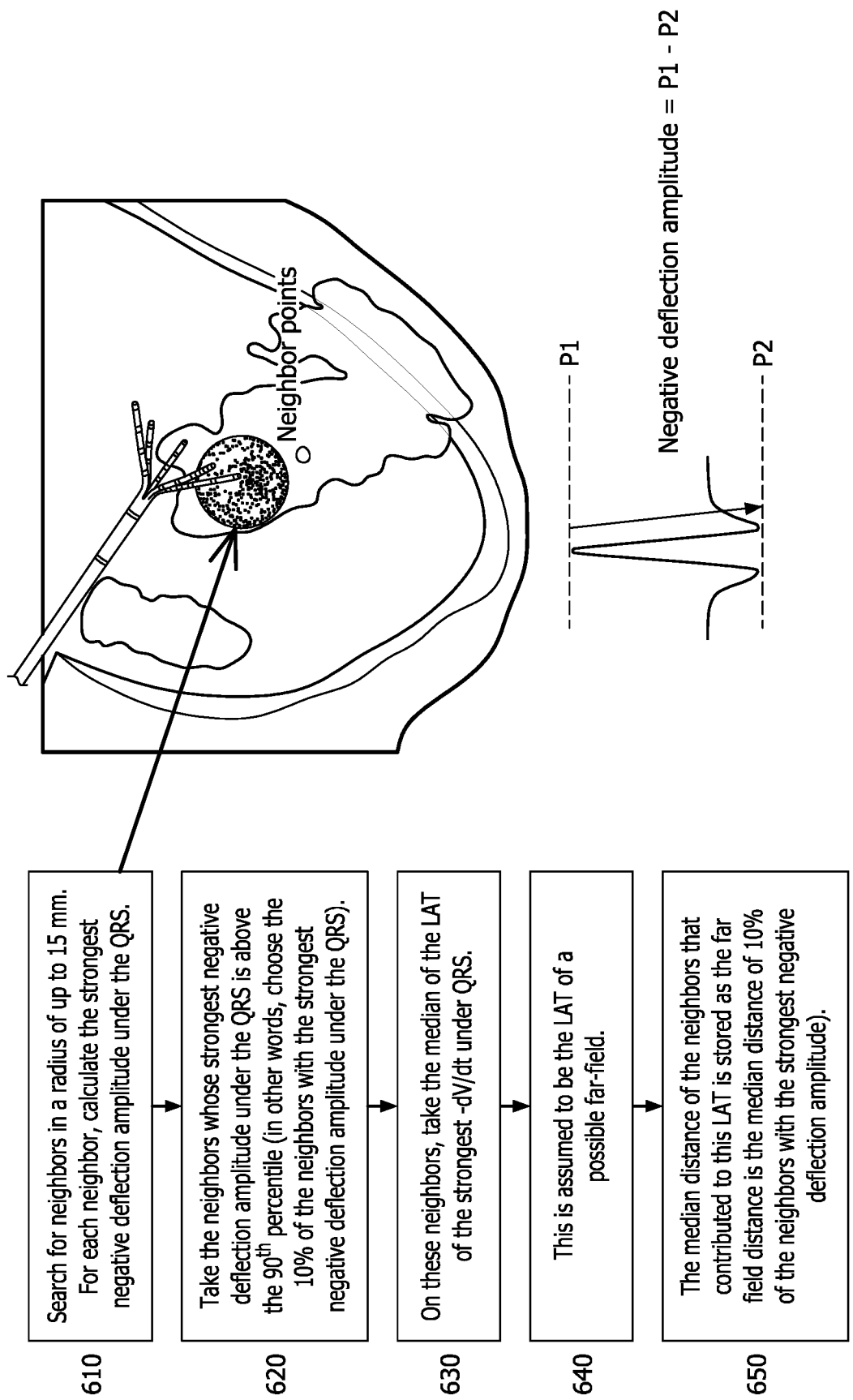
FIG. 6. is a diagram for identifying neighboring abnormal activity.

As shown in FIG. 6, neighboring points effected by a far field may be removed from the determination of neighboring points at step 230 of the process 200 of FIG. 2. The far field effected neighboring points may be determined by detecting neighboring points within a given radius (e.g., 15 mm) from the seed point at 610. For each neighboring point within the given radius, the strongest negative deflection amplitude under the QRS may also be determined at 610. An upper value (e.g., 90th percentile) of the strongest –dV/dt of the neighbors, where the strongest –dV/dt is under the QRS, may be determined at 620. At 630, a median value of the LAT values of the strongest –dV/dt under the QRS may be identified and this median value may be assumed to be the LAT value of a possible far field at 640. At 650, the median distance of the neighboring points that contribute to the LAT value determined at 640 may be stored as the far field distance such that the far field distance is the median distance of a percent (e.g., 10%) of the neighboring point with the strongest negative deflection amplitude.

Figure 7:
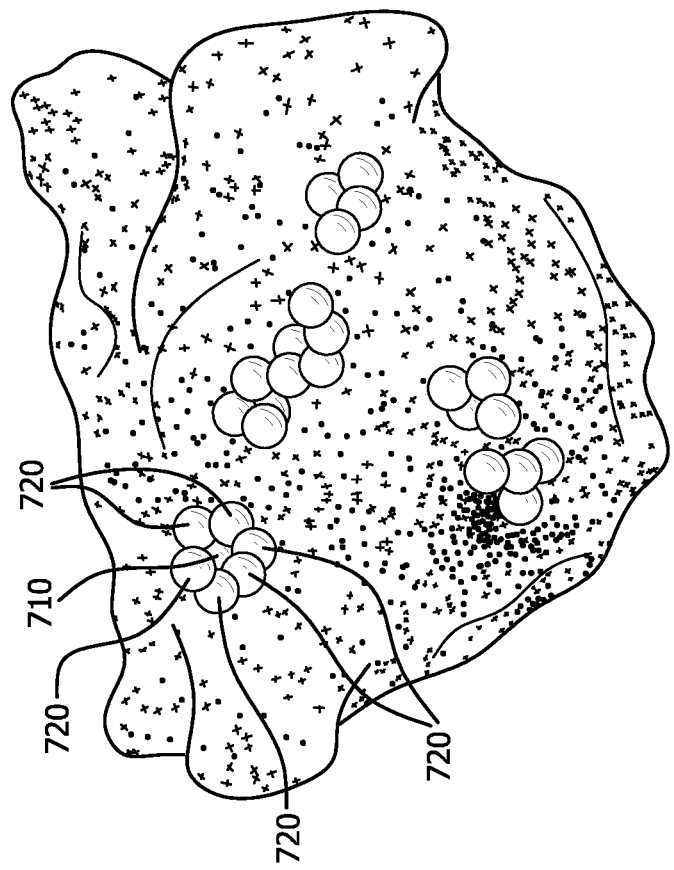
FIG. 7A is a diagram for identifying seed points of abnormal activity.
FIG. 7B is a diagram for identifying neighboring points of abnormal activity.

FIG. 7A shows a diagram of identified seed points 710 with a high specificity, as determined based on step 210 of process 200 of FIG. 2. FIG. 7B shows a diagram of identified neighboring points 720 with electrical activations at similar times as the seed points 710 of FIG. 7A, as determined based on steps 220-240 of process 200 of FIG. 2. Notably, the seed points 710 are LAVA points with a high specificity and the neighboring points 720 allow for increased sensitivity and have electrical activations at a similar time as the respective seed points 710.

Figure 8:
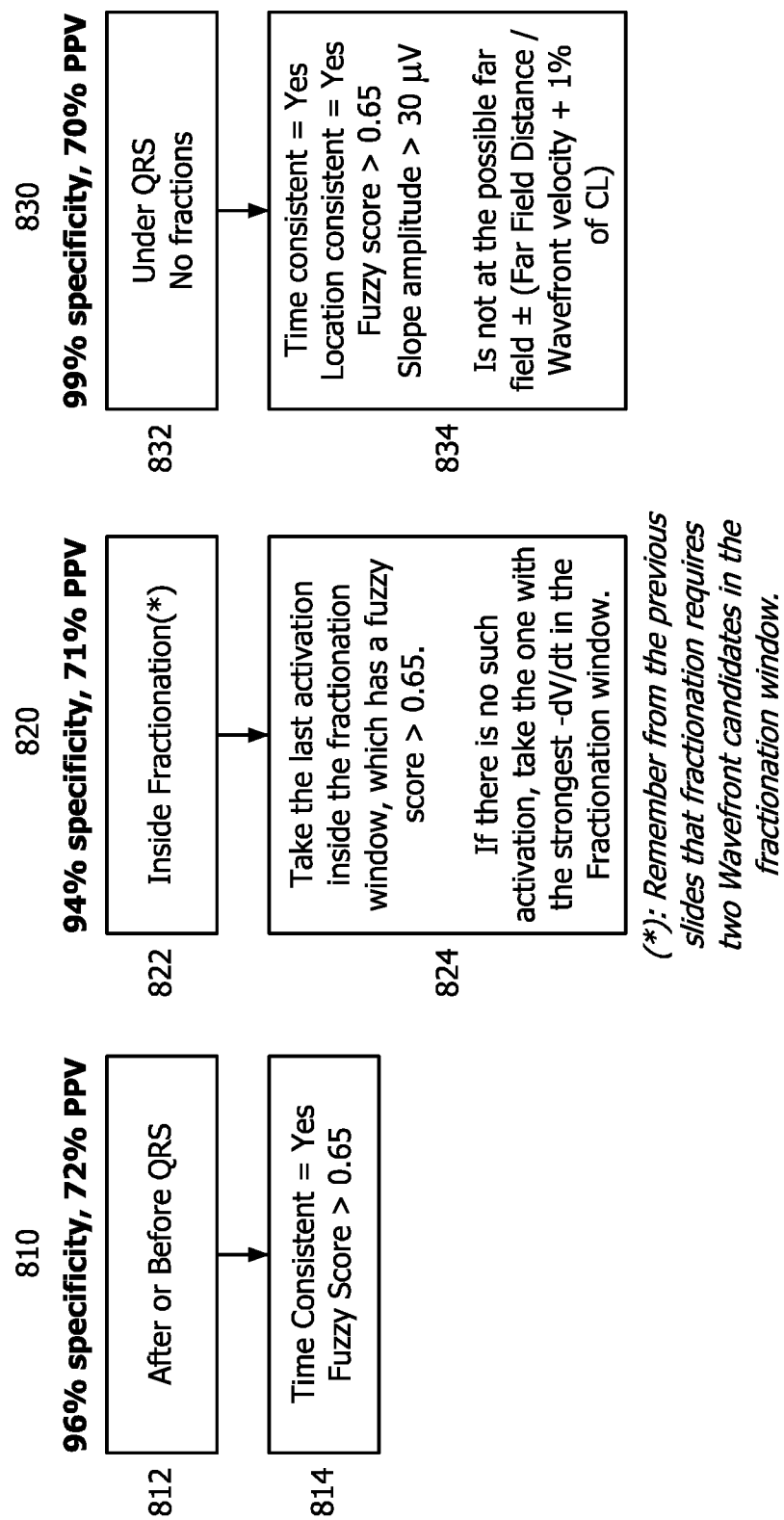
FIG. 8 is a diagram for identifying seed points of abnormal activity.

FIG. 8 shows variations 810, 820, and 830 for determining the seed points based on step 210 of the process 200 of FIG. 2. The conditions for the temporally latest variation (i.e., from variation 810, 820, and 830) to be met may be applied when identifying a seed point. The variations 810, 820, and 830 may utilize the outputs of the QRS detection 410, wavefront activations 420 and fractionation detection 430 of FIG. 4 as inputs.

At variation 810, a seed point may be identified if the conditions 812 and 814 are met. As shown, a seed point may be identified at variation 810 if the corresponding electrical activity is exhibited after or before QRS, at 812, if time consistency, as discussed in reference to FIG. 5, is present, and if the fuzzy score corresponding to the electrical activity is greater than a threshold fuzzy score (e.g., 0.65), at 814. A seed point identified based on variation 810 may, for example, have a specificity of 96% and a positive predictive value (PPV) of 72%.

At variation 820, a seed point may be identified if the conditions 822 and 824 are met. At 822, a determination may be made if electrical activation at a given point is inside a fractionation window (e.g., if at least two wavefront candidates are present within a fractionation window). At 824, the seed point may be determined based on the last activation inside the fractionation window, which has a fuzzy score of greater than a threshold fuzzy score (e.g., 0.65) and if no such activation is present, then the seed point may be determined based on the strongest –dV/dt in the fractionation window. A seed point identified based on variation 820 may, for example, have a specificity of 94% and a PPV of 71%.

At variation 830, a seed point may be identified if the conditions 832 and 834 are met. At 832, a determination may be made if the electrical activation at a given seed point is under QRS and is not within a fractionation window. At 834, the seed point may be determined if the electrical activation at the given point is time consistent, as disclosed herein, if the electrical activation is location consistent with neighboring points, if the fuzzy score is above a threshold fuzzy score (e.g., 0.65), if the slope amplitude between a positive amplitude and an adjacent negative amplitude of a ECG signal (i.e., the negative deflection amplitude) is greater than a given voltage (e.g., 30 µV), and if the electrical activation at the given point is not a possible far field effect as determined by, for example ((Far Field Distance/Wavefront velocity)+1% of CL). A seed point identified based on variation 830 may, for example, have a specificity of 99% and a PPV of 70%.

FIG. 9 shows a process 900 for determining the abnormal neighboring points based on steps 220-240 of the process 200 of FIG. 2. Notably, the process 900 may allow for increased sensitivity. At step 910 of the process 900, points within a given radius (e.g., 12 mm) from a seed point may be identified. At 920, a determination whether location consistency exists between the seed point and each of the points identified in step 910 may be made, as described in relation to FIG. 5. To clarify, the distance between each neighboring point and the seed point may be divided by the wavefront velocity (e.g., 0.5 mm/ms). A variance may be added to the resulting time (e.g., 1% of the CL). At step 930, a fuzzy score for points for which there is an activation within the time determined by at step 920 may (i.e., where location consistency is present) be determined. At step 930, points for which the fuzzy score exceeds a threshold fuzzy score (e.g., 0.65) may be identified. At step 940, the slope amplitude of the electrical activity for points for which the fuzzy score exceeds the threshold fuzzy score may be identified. The points that have a slope amplitude that exceeds a threshold slope amplitude (e.g., 30 µV) may be determined to be abnormal neighboring points. As noted at step 950, if there are more than more than one activation at a given point that satisfy the steps 910-940, then the latest of such activations may be applied when determining the abnormal neighboring points.

Figure 10:
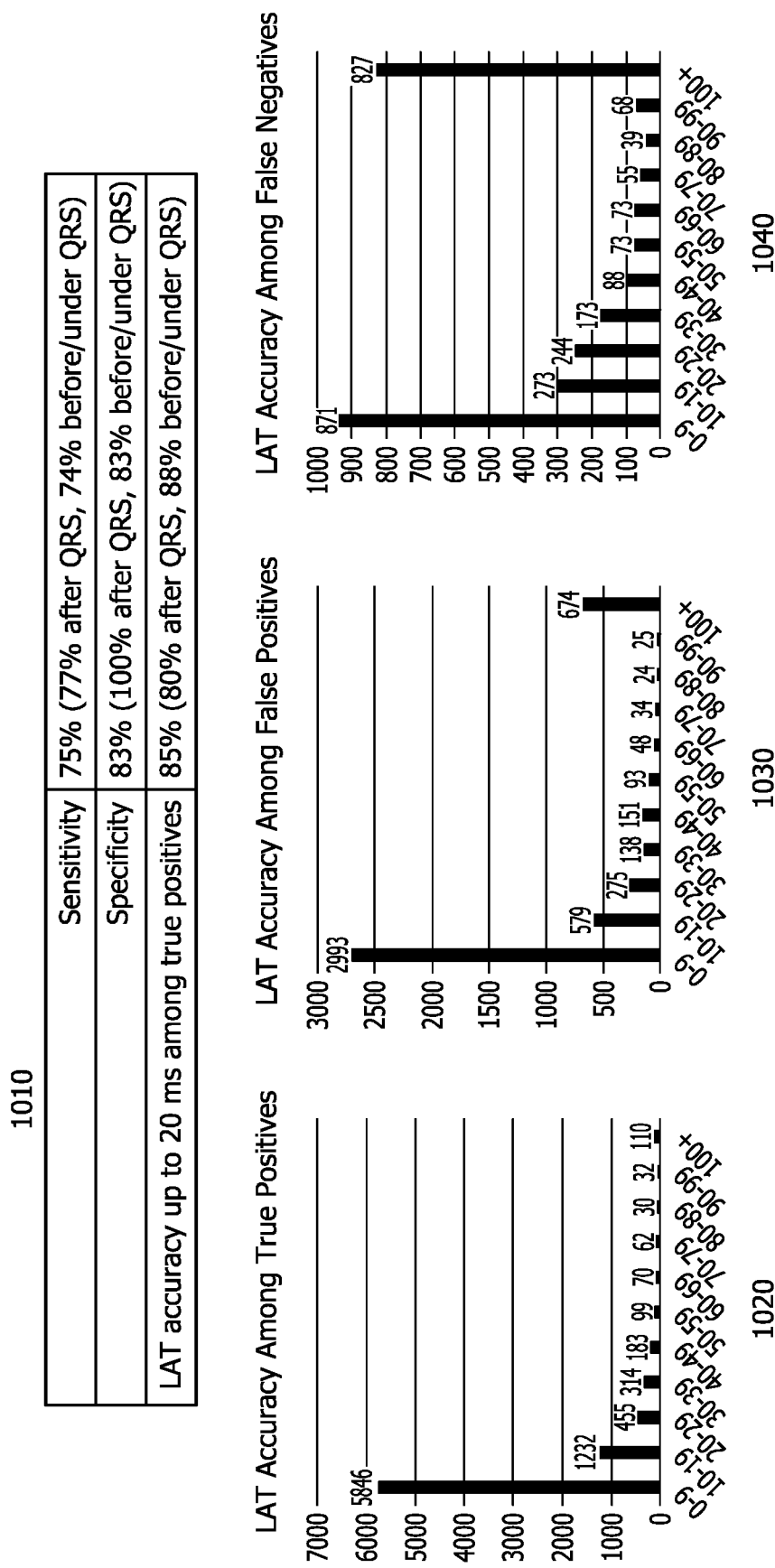
FIG. 10 are experimental results of the techniques implemented in accordance with subject matter disclosed herein.

FIG. 10 shows the experimental results of applying the process 200 of FIG. 2 in accordance with FIGS. 3-9. FIG. 10 is based on the result of a dataset fifteen unique cases and the analysis a total of 41,953 points in accordance with the subject matter disclosed herein. As shown in table 1010, an average sensitivity of 75% (77% after QRS, 75% before/under QRS) was exhibited across the dataset. An average specificity of 83% (100% after QRS, 83% before/after QRS) was exhibited across the dataset. As noted, the results in table 1010 are provided assuming that the physician is interested in LAVAs in areas of up to 1.5 mV peak-to-peak bipolar amplitudes. A LAT accuracy of up to 20 ms among true positives was exhibited for 85% (80% after QRS, 88% before/under QRS) for the data set. Chart 1020 shows the LAT accuracy among true positives. Chart 1030 shows the LAT accuracy among false positives. Chart 1040 shows the LAT accuracy among false negatives.

Any of the functions and methods described herein can be implemented in a general-purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer-readable media). The results of such processing can be maskworks that are then used in a semiconductor manufacturing process to manufacture a processor which implements features of the disclosure.

Any of the functions and methods described herein can be implemented in a computer program, software, or firmware incorporated in a non-transitory computer-readable storage medium for execution by a general-purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

The invention claimed is:

1. A method for identifying abnormal activations in intra-cardiac electrograms, the method comprising:
   identifying a seed point, based on a high specificity, with abnormal activations at a first time;
   identifying at least one neighboring point proximate to the seed point;
   determining a sensitivity of the at least one neighboring point, wherein the sensitivity is determined by determining that the at least one neighboring point exhibits activations at a similar time as the first time; and
   identifying the neighboring point as an abnormal neighboring point based on determining that the neighboring point exhibits activations at a similar time as the first time.

2. The method of claim 1, further comprising receiving and using input information, the input information comprising one or more of a bipolar ECG of a mapping channel, a distal and proximal unipolar ECG of a mapping channel, a lead body surface ECG, and an intra-cardiac spatial information.

3. The method of claim 2, further comprising providing the input information to one or more analysis modules, the analysis modules comprising one or more of a QRS detection module, wavefront activations module, fractionation detecting module, and a local abnormal ventricular activation (LAVA) logic module.

4. The method of claim 3, wherein the seed point is identified based on an output of the one or more analysis modules.

5. The method of claim 3, wherein the QRS detection module comprises one or more of a pre-processing operations and a QRS detection logic operation.

6. The method of claim 5, wherein the QRS detection logic operation outputs a start of QRS and an end of QRS.

7. The method of claim 3, wherein the wavefront activations module comprises one or more of a preprocessing operations, a wavefront logic operation, a feature extraction operation, and a fuzzy logic operation.

8. The method of claim 3, wherein the wavefront activations module outputs one or more sets of timestamps and fuzzy scores.

9. The method of claim 3, wherein the fractionation detection module outputs an interval comprising a start of fractionation and an end of fractionation.

10. The method of claim 1, wherein determining at least one of the seed points and the neighboring point is based on one or more of a fuzzy score, a time consistency and a location consistency.

11. The method of claim 10, wherein the time consistency is based on identifying the abnormal activations at a previous activation within a deviation tolerance based on a cycle length.

12. The method of claim 10, wherein the location consistency is based on a determination of a distance between the seed point and the neighboring point divided by a wavefront velocity.

13. The method of claim 12, wherein the location consistency is further based on a deviation tolerance based on a cycle length.

14. The method of claim 1, further comprising identifying a far field distance.

15. The method of claim 14, further comprising determining that at least one neighboring point of the neighboring points is within the far field distance and identifying the neighboring point within the far field distance as a far field neighboring point.

16. The method of claim 1, wherein the seed point is determined based on one or more of a QRS time, time consistency, fuzzy score, fractionation period, and slope amplitude.

17. The method of claim 1, wherein the at least one neighboring point is within 12 mm from the seed point.

18. The method of claim 1, wherein identifying the neighboring point as an abnormal neighboring point is based on one or more of a location consistency between the seed point and the neighboring point, a fuzzy score, and a slope amplitude.

19. An apparatus for identifying abnormal activations in intracardiac electrograms, the apparatus comprising:
    a memory; and
    a processor operatively coupled with the memory and in communication with the memory, the processor configured to:
        identify a seed point with abnormal activations at a first time, based on a high specificity;
        identify at least one neighboring point proximate to the seed point;
        determine that the neighboring point exhibits activations at a similar time as the first time; and
        identify the neighboring point as an abnormal neighboring point based on determining that the neighboring point exhibits activations at a similar time as the first time.

20. A non-transitory computer-readable medium for identifying abnormal activations in intracardiac electrograms, the non-transitory computer-readable medium having instructions recorded thereon, that when executed by the processor, cause the processor to perform operations including:
    identifying a seed point with abnormal activations at a first time, based on a high specificity;
    identifying at least one neighboring point proximate to the seed point;
    determining that the neighboring point exhibits activations at a similar time as the first time; and
    identifying the neighboring point as an abnormal neighboring point based on determining that the neighboring point exhibits activations at a similar time as the first time.

* * * * *